United States Patent
Tanhehco et al.

(10) Patent No.: US 6,739,338 B2
(45) Date of Patent: May 25, 2004

(54) NEO-NATAL OXYGEN DELIVERY SYSTEM (75) Inventors: Benito L. Tanhehco, Powell, TN (US); Shelia D. Ware, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 90 days.

(21) Appl. No.: 10/137,259

(22) Filed: May 2, 2002

(65) Prior Publication Data

US 2002/0153011 A1 Oct. 24, 2002

Related U.S. Application Data (63) Continuation of application No. 09/543,656, filed on Apr. 5, 2000, now abandoned.

(51) Int. Cl.$^7$ ................................................. A62B 9/02
(52) U.S. Cl. .......................... 128/205.24; 128/204.18; 128/203.16
(58) Field of Search .................. 128/201.28, 204.18, 128/205.11, 205.24, 207.12, 207.14–207.18, 200.14–200.24, 203.23, 203.16, 203.12; 664/30–35, 118–129, 902, 19, 82, 92; 606/1; 239/338, 343, 370

(56) References Cited

U.S. PATENT DOCUMENTS

| | | | |
|---|---|---|---|
| 4,451,257 A | 5/1984 | Atchley | |
| 4,848,333 A | 7/1989 | Waite | |
| 4,886,055 A | 12/1989 | Hoppough | |
| 4,919,132 A | * 4/1990 | Miser | 128/205.17 |
| 5,036,847 A | 8/1991 | Boussignac et al. | |
| 5,076,787 A | 12/1991 | Overmyer | |
| 5,538,002 A | 7/1996 | Boussignac et al. | |
| 5,694,923 A | 12/1997 | Hete et al. | |
| 5,720,276 A | 2/1998 | Kobatake et al. | |
| 5,878,743 A | 3/1999 | Zdrojkowski et al. | |
| 5,896,857 A | 4/1999 | Hely et al. | |

OTHER PUBLICATIONS

Abstract of Japanese Unexamined Patent No. 62–140026 dated Jun. 23, 1987.
Copy of brochure of Hudson RCI® Concha Thermo® IV Heated Humidifier Catalog No. 400–00 dated 08/96.

\* cited by examiner

*Primary Examiner*—Glenn K. Dawson
(74) *Attorney, Agent, or Firm*—Luedeka, Neely & Graham PC (57) ABSTRACT

A system for delivering warm, humidified oxygen to patients at very low flow rates, the system including a conduit having an inlet connected to a source of humidified oxygen at a first flow rate and an outlet end for delivering humidified oxygen to a patient at a second flow rate that is less than the first flow rate. A first flowpath extends through a sidewall of the conduit for continuously bleeding oxygen from the conduit and a second flowpath extends through the sidewall of the conduit downstream from the first flowpath for continuously bleeding oxygen from the conduit at a rate of from about 0 liters/minute or above. A substantially solid member is movably positionable adjacent the second flowpath for selectively blocking and unblocking portions of the second flowpath for defining a variably dimensionable flow path in order to control over the amount of oxygen flowing through the second flowpath.

1 Claim, 12 Drawing Sheets

FIG. 37c

NEO-NATAL OXYGEN DELIVERY SYSTEM

CROSS-REFERENCE TO RELATED APPLICATION

This application is a continuation of co-pending application Ser. No. 09/543,656, filed Apr. 5, 2000, and entitled NEO-NATAL OXYGEN DELIVERY SYSTEM, now abandoned.

FIELD OF THE INVENTION

This invention relates generally to devices for supplying fluids to patients and more particularly to devices for supplying warm, humidified oxygen gas to patients.

BACKGROUND AND SUMMARY OF THE INVENTION

Oxygen is commonly delivered in the practice of medicine to patients as a gas. The oxygen flows from a source to a delivery device such as a nasal cannula, for delivery to the patient's respiratory tract.

The administration of oxygen to patients, including neonatal, pediatric and elderly patients, requires the selection of an oxygen delivery system that suits the patient's size, needs and therapeutic result. Typically, the oxygen gas delivered directly from a hospital oxygen delivery system is dry and cold. Delivering dry and cold oxygen to an infant, for example, can undesirably lower body temperature and promote dehydration. Accordingly, it is often preferred to warm and humidify the oxygen so that the patient inhales a warm gas-liquid mixture.

It has proved difficult to supply warm oxygen having sufficient humidity at flow rates of less than about 2 liters/minute. Standard equipment available for both warming and humidifying oxygen is suitable for use with adults and is adjustable to deliver a volumetric fluid flow of from about 2 to about 15 liters per minute. These devices, however, generally require a minimum flowrate of at least about 2 liters per minute in order to operate. Pediatric patients, particularly neonatal patients, require a flow rate of less than about 2 liters per minute, sometimes only slightly above zero liters per minute (e.g. about ⅛ liter per minute).

Accordingly, there is a need in the art for a device which enables warm, humidified oxygen to be supplied to pediatric/infant patients at flow rates of from about 2 liters per minute and below.

It is therefore an object of the invention to provide a system for controlling the flow rate of fluid, such as warm, humidified oxygen, from a fluid source.

An additional object of the invention is to provide a system of the character described that is compatible with existing equipment, such as oxygen humidifiers.

A further object of the invention is to provide a system of the character described that is suitable for use with pediatric patients.

It is another object of the invention to provide a system of the character described that is selectively adjustable to enable an oxygen flow rate of from about 0 to about 2 liters per minute.

A further object of the invention is to provide a system of the character described that is uncomplicated in configuration and convenient to use.

A still further object of the invention is to provide a system of the character described that is economical and suitable for use with conventional oxygen delivery systems.

With regard to the foregoing, the present invention is directed to a system for use with standard humidification equipment having a flow rate of at least about 3 liters/minute for delivering fluids such as oxygen, preferably warm, humidified oxygen to patients at a flow rate of from about 0 to about 2 liters/minute. As used herein, the term "warm/humidified oxygen" refers to oxygen gas having a temperature of from about 30° C. to about 37° C. (about 86° F. to about 98.6° F.) and a relative humidity of from about 80 to about 100%.

The system includes a conduit having an inlet connected to a source of humidified oxygen at a flow rate of at least about 3 liters/minute and an outlet end for delivering humidified oxygen to a neo-natal patient at a flow rate of from about 0 to about 2 liters/minute. A first aperture extends through the sidewall of the conduit for bleeding oxygen from the conduit so that the flow in the conduit is reduced to about 2 liters/minute. A second aperture is provided downstream from the first aperture and extends through the sidewall for bleeding oxygen from the conduit at a rate of from about 0 to about 2 liters/minute. A substantially solid member is movably positionable adjacent the second aperture for defining a variably dimensionable flow path to enable control over the amount of oxygen bled through the second aperture.

In another embodiment, the invention is directed to a system for controlling the flow rate of fluid from a fluid source, such as humidified oxygen, for delivery to a patient.

In a preferred embodiment, the system includes a conduit having an interior and an exterior separated by a substantially continuous sidewall, an inlet end in flow communication with an outlet end for flow of fluid from the fluid source through the conduit from the inlet end toward the outlet end, the inlet end being in flow communication with the source of fluid at a first flow rate and the outlet end being in flow communication with a fluid delivery device for delivering fluid to the patient at a second flow rate that is lower than the first flow rate.

A first aperture extends through the sidewall for passage of fluid from the interior to atmospheric regions adjacent the exterior of the conduit and for reducing the flow rate of fluid within the conduit to a third flow rate that is less than the first flow rate and greater than or equal to the second flow rate. A second aperture is provided downstream from the first aperture extends through the sidewall. A substantially solid member is movably positionable adjacent the second aperture for defining a variably dimensionable flow path for passage of fluid from the interior to atmosphere regions adjacent the exterior of the conduit. Variation of the dimension of the variably dimensionable flow path selectively enables escape of fluid from the interior of the conduit to provide the second flow rate of fluid.

In another embodiment, the invention relates to a system for delivering humidified oxygen to a patient. The system preferably includes a conduit having an inlet connected to a source of humidified oxygen at a first flow rate and an outlet end for delivering humidified oxygen to a patient at a second flow rate that is less than the first flow rate. A first flowpath extends through a sidewall of the conduit for continuously bleeding oxygen from the conduit. A second flowpath is located downstream from the first flowpath and extends through the sidewall of the conduit for continuously bleeding oxygen from the conduit at a rate of from about 0 liters/minute or above. A substantially solid member is movably positionable adjacent the second flowpath for selectively blocking and unblocking portions of the second flowpath for defining a variably dimensionable flow path in order to control over the amount of oxygen flowing through the second flowpath.

In yet another aspect, the invention relates to a method for delivering treatment fluids, such as humidified oxygen, to pediatric patients from a source of fluid of the type used for adults and having a flow rate above about 3 liters per minute. The method includes the steps of providing the oxygen source, placing it in flow communication with a delivery system in accordance with the invention and manipulating the delivery system to achieve a desired flow rate to the patient of from about 0 to about 2 liters per minute.

The invention advantageously enables warm, humidified oxygen to be delivered at low flow rates heretofore unobtainable by conventional hospital equipment. The invention thus enables the use of standard oxygen and other delivery and humidification systems in the treatment of pediatric and other patients having treatment flow rate requirements below those available from standard treatment equipment. The system also advantageously adapts to fit pediatric output components, such as pediatric cannulas having smaller tubing size, while connecting to adult or standard input components having larger tubing sizes.

BRIEF DESCRIPTION OF THE DRAWINGS

The above and other features and advantages of the present invention will become further known from the following detailed description considered in conjunction with the accompanying drawings in which.

DETAILED DESCRIPTION

Figure 1:
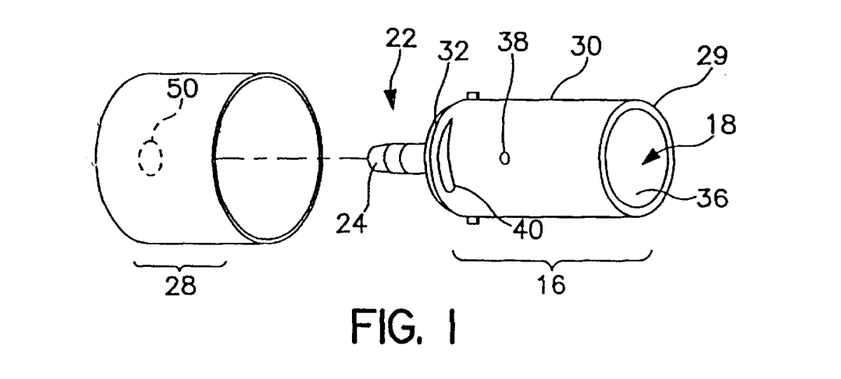
FIG. 1 is an exploded perspective view of a preferred embodiment of a flow control device in accordance with the invention.
Figure 2:
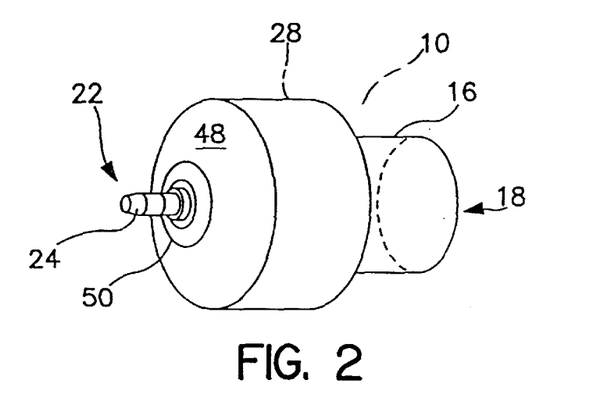
FIG. 2 is a perspective view of the device of FIG. 1 in an assembled state.
Figure 3:
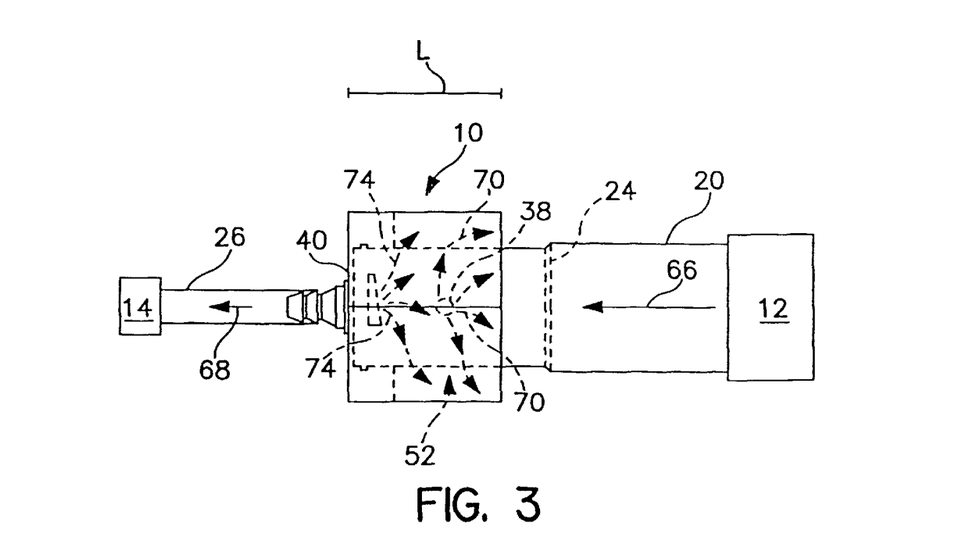
FIG. 3 is a plan view of an oxygen delivery system utilizing the device of FIG. 1.

With initial reference to FIGS. 1–3, there is shown a system 10 for controlling the flow rate of fluid, such as a gas-liquid mixture, in flow communication with a source of fluid, such as a source of warm, humidified oxygen 12. The system 10 is available to deliver the flow of warm, humidified oxygen to a pediatric or infant patient as by a pediatric or infant sized nasal cannula 14. Each component of the system 10 is preferably made of a plastic material, such as polyethylene and manufactured using extrusion, blow molding or thermo-forming techniques.

As noted previously, the term "warm/humidified oxygen" refers to oxygen gas having a temperature of from about 30° C. to about 37° C. (about 86° F. to about 98.6° F.) and a relative humidity of from about 80 to about 100%. A preferred source of warm/humidified oxygen is provided by flowing hospital grade oxygen through a heated humidifier available under the trade name ConchaTherm IV from Hudson RCI of Temecula, Calif. The instruction manual for the ConchaTherm IV states that it requires a flow rate of 2 liters per minute or greater to prevent overheating of its electronic circuitry.

To avoid problems associated with circuit overheating and the like, it is desirable to operate the humidifier at a setting above its lowest possible setting. Accordingly, it is preferred that when the ConchaTherm IV humidifier is used as a source of warm, humidified oxygen, that it be operated at a flowrate of from about 3 to about 15 liters per minute, most preferably from about 6 to about 10 liters per minute. The system of the present invention enables these flowrates to be reduced to flowrates suitable for pediatric or infant patients, i.e. from about slightly above 0 liters per minute, such as about ⅛ liter per minute, to about 2 liters per minute.

The system 10 includes flow member 16 having an open inlet end 18 placeable in flow communication with the source of humidified oxygen 12 as by tubing 20 opposite an outlet end 22 in flow communication with a fitting 24 and placeable in flow communication with the cannula 14 as by tubing 26. A control member 28 cooperates with the flow member 16 for adjustably controlling the flow of humidified oxygen out of the fitting 24. The fitting 24 is sized to cooperate with pediatric sized delivery apparatus, i.e., pediatric tubing, cannulas and the like, while the inlet end 18 is sized to cooperate with the tubing 20 for flow communication of the oxygen from standard source apparatus, such as the ConchaTherm IV humidifier. In this regard, the end 18 may include flange 29 for snugly engaging the tubing 20.

Figure 4:
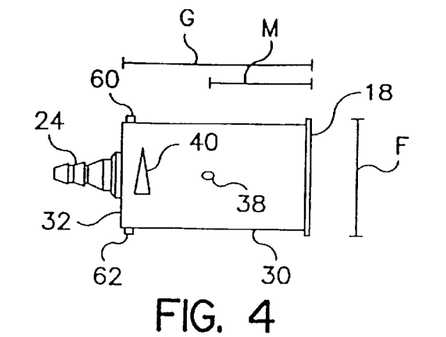
FIG. 4 is a side plan view of a flow member component of the device of FIG. 1.
Figure 5:
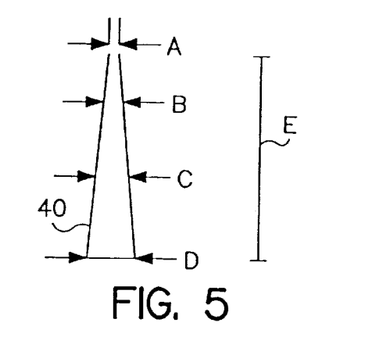
FIG. 5 is an enlarged view of a portion of the component of FIG. 4.
Figure 6:
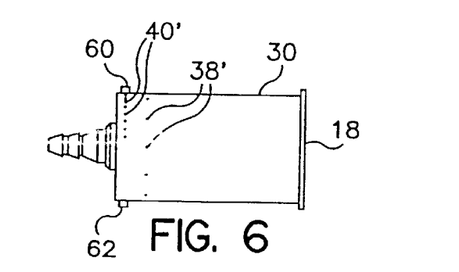
FIG. 6 is a side plan view of an alternate embodiment of the component of FIG. 4.

With additional reference now to FIGS. 4–6, the flow member 16 is preferably provided by a conduit 30, an open first end of which provides the inlet end 18. The opposite end of the conduit 30 is closed, as by end wall 32. The fitting 24 extends through the end wall 32 to provide a path for flow of the oxygen. The conduit 30 is preferably cylindrical and includes cylindrical sidewall 36. The cylindrical sidewall 36 is substantially solid with the exception of an aperture 38 and an aperture 40 which are spaced apart from one another and extend through the sidewall 36. The aperture 38 is preferably upstream of the aperture 40 or located between the aperture 40 and the inlet end 18 and is preferably a circular aperture. The aperture 40 is preferably a triangular shaped aperture, as best seen in FIG. 5.

In another embodiment shown in FIG. 6, the aperture 38 is provided by a plurality of apertures 38' and the aperture 40 is provided by a plurality of apertures 40'. Each aperture 38' is preferably in alignment with each other aperture 38' and each aperture 40' is preferably aligned with each other aperture 40' around the periphery of the sidewall 36.

Figure 7:
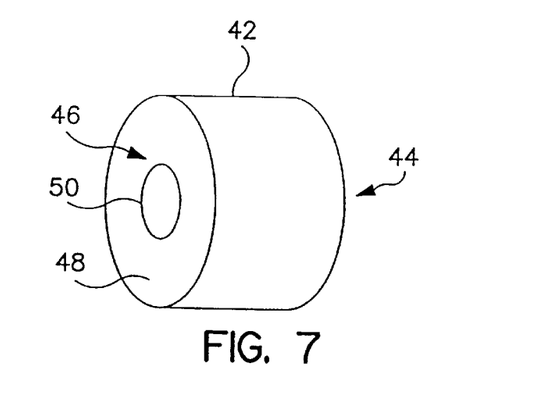
FIG. 7 is a perspective view of a flow control component of the system of FIG. 1.
Figure 8:
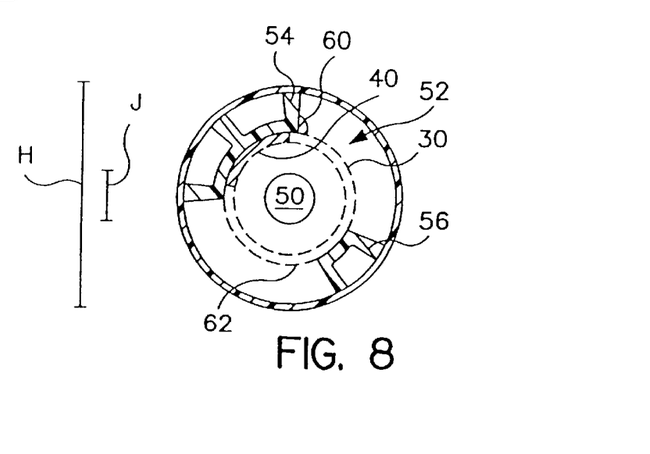
FIG. 8 is an end view of the system of FIG. 1 showing the relationship between a flow component and a control component.
Figure 9:
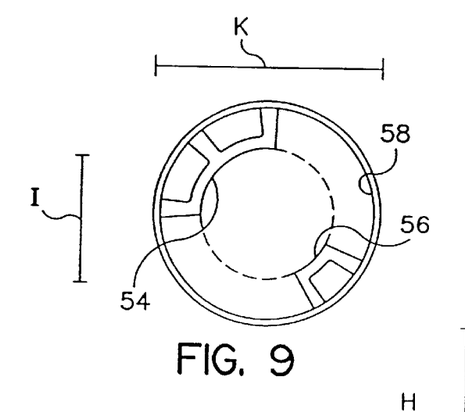
FIG. 9 is an inlet end view of the component of FIG. 7.

With additional reference to FIGS. 7–9, the control member 28 includes a cylindrical member 42 having an open end 44 opposite a closed end 46. The closed end 46 is preferably provided as by a circular end wall 48 enclosing the end of the cylindrical member 42. The end wall 48 includes an aperture 50 centrally located and sized to receive the fitting 24 in a snap-fit relationship to maintain the control member 28 and the flow member 16 closely adjacent one another. The diameter of the cylindrical member 42 is greater than that of the cylindrical member 30 to enable the cylindrical member 42 to receive the cylindrical member 30, preferably sized to provide an annular area 52 there between (FIGS. 3 and 8) having a width sufficient to enable the flow of warm, humidified oxygen from the cylindrical member 30 through the apertures 38 and 40.

As shown in FIGS. 8 and 9, the control member 28 preferably includes projections 54 and 56 which extend from interior sidewall 58 of the cylindrical member 42 and rotatably engage opposite sides of the exterior of the cylindrical member 30. The projection 56 is opposite the projection 54 so that a portion of the cylindrical member 30 is captured there between. The rotation of the cylinders 30 and 43 is preferably limited as by stops 60 and 62 located on the exterior of the cylindrical member 30 for engaging the outside edges of the projection 54 or the projection 56, as may be preferred. The stops 60 and 62 are preferably located such that contact with the stop 60 defines the position of the projection 54 when it fully blocks or sealingly covers the aperture 40 against flow there through and contact with the stop 62 defines the position of the projection 54 when it fully clears or opens the aperture 40 for flow there through.

Figure 10:
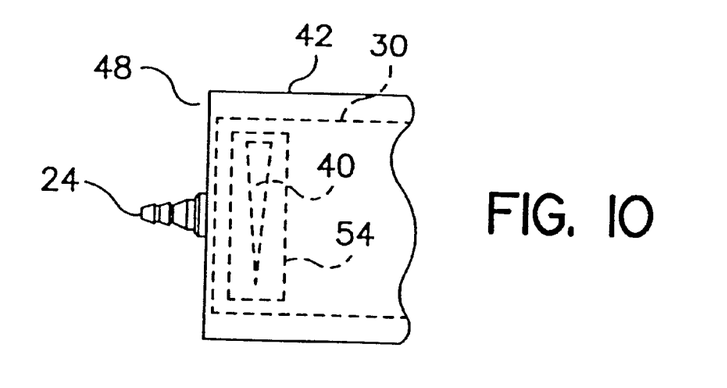
FIG. 10 is an enlarged side plan view of a portion of the system of FIG. 1 showing a control member fully blocking an aperture.
Figure 11:
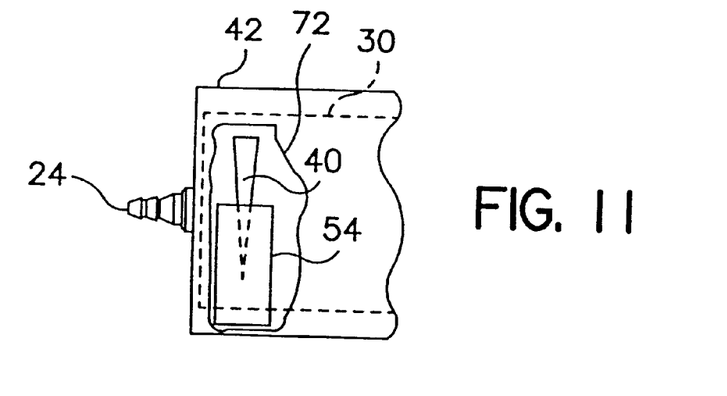
FIG. 11 is an enlarged side plan view of a portion of the system of FIG. 1 showing a control member partially blocking an aperture.
Figure 12:
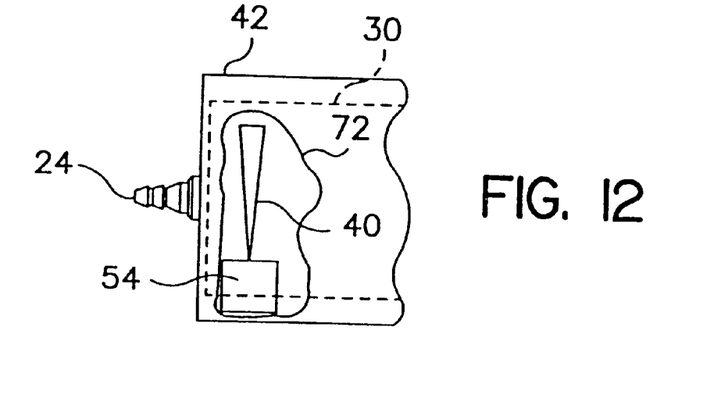
FIG. 12 is an enlarged side plan view of a portion of the system of FIG. 1 showing an aperture in an unblocked state.

As best seen in FIGS. 10–12, the cylindrical member 42 and the cylindrical member 30 are rotatable relative to one another so that the projection 54 may be positioned to be clear of the aperture 40, partially block the aperture 40 or completely block the aperture 40. In this regard, the apertures 38 and 40 (and the apertures 38' and 40') function to enable the inlet flow of humidified oxygen, represented by the arrow 66 (FIG. 3) to be altered to provide a desired outlet flow of humidified oxygen, represented by the arrow 68, to the patient.

For example, standard equipment available for warming and humidifying oxygen is generally not suitable for use with pediatric patients, particularly neonatal patients, who require treatment rates of less than about 2 liters per minute, sometime only slightly above zero liters per minute. The system 10 is suitable for use with standard humidification equipment, such as the ConchaTherm IV described above, and is adjustable to control humidified oxygen available at a flow of from about 3 to about 15 liters per minute in order to provide delivery of humidified oxygen at a flow rate of from about 0 liters per minute to about 2 liters per minute. It will be understood, however, that the invention may be configured to yield various desired flow rates from a given flow source.

For example, as described herein the aperture 38 is sized to reduce the flow rate in the cylindrical member 30 from an input flow rate from the humidifier of about 8 liters per minute to a maximum flow rate in the cannula 14 of about 2 liters per minute or less. In this case, the aperture 38 provides a passage sized to leak a flow rate of about 6 liters per minute there through and into the annular area 52 and out of the open end 44 to the surrounding atmosphere, as represented by the arrows 70. In this regard, it will further be appreciated that the cylindrical member 42 also serves to expand, deflect and muffle the flow represented by the arrows 70 to minimize noise and directional air flow which might disturb the patient.

The aperture 40 and the projection 54 cooperate to enable the flow rate 68 to be maintained at about 2 liters per minute, adjusted to about 0 liters per minute or reduced to a desired flow rate within this range. When the aperture 40 is fully blocked by the projection 54 as shown in FIG. 10, the flow rate 68 will be about 2 liters per minute, as flow will not be conducted from the conduit 30 through the aperture 40. When the aperture 40 is partially blocked by the projection 54, as shown in FIG. 11 with a portion 72 of the cylindrical member 42 cut away, a flow indicated by arrows 74 travels from the conduit 30 there through in the manner of the flow 70, reducing the flow indicated by arrow 68 delivered to the patient to a rate of less than about 2 liters per minute and greater than about 0 liters per minute. The degree of blockage of aperture 40 can be adjusted to provide any desired flow rate within this range. When the projection 54 is fully clear of the aperture 40, as shown in FIG. 12, the flow 74 will be about 2 liters per minute such that the flow 68 will be about 0 liters per minute.

A pressure gauge or meter may be connected in line with the tubing 68 and/or the system may be calibrated prior to use to facilitate delivery of desired oxygen flow rates to the patient. For example, to calibrate the system, a flow meter may be connected in place of the cannula 14 and the dimension of the aperture 40 adjusted as previously described. The rotational position of the flow control member may be recorded against the flow rate 68 measured by a flow meter. In this regard, indicia such as symbols designating open and closed and gradations there between (e.g., ¼, ½, ¾, etc.) may be provided around the circumference of the control member and a corresponding mark or indicia provided on the flow member 16 to indicate the relative dimension of the aperture in terms of blockage by the projection 54 or other indicia corresponding to the flow rate.

For the purpose of an example, the system 10 is preferably dimensioned as set forth in Table 1 for use in delivering a flow rate of from about 0 to about 2 liters per minute when used with an oxygen humidifier capable of providing warm, humidified oxygen at an output of about 6 liters per minute.

TABLE 1

| Dimension | Distance (inches/cm) |
| --- | --- |
| A (FIG. 5) | 0.001 |
| B (FIG. 5) | 0.015 |
| C (FIG. 5) | 0.033 |
| D (FIG. 5) | 0.055 |
| E (FIG. 5) | 105° (0.878 inch dia.) |
| F (FIG. 4) | 0.870 inch dia. |
| G (FIG. 4) | 1.50 |
| H (FIG. 8) | 2.00 |
| I (FIG. 9) | 0.878 inch dia |
| J (FIG. 9) | 0.166 |
| K (FIG. 9) | 2.00 |
| L (FIG. 3) | 1.06 |
| M (FIG. 4) | 0.80 |
| Aperture 3 8 | 0.040 dia. |

Turning now to FIGS. 13–19, there is shown another embodiment of a system 100 for controlling the flow rate of fluid, such as a gas-liquid mixture, from a source of fluid, such as a source of warm, humidified oxygen for delivery to a patient as by a nasal cannula.

Figure 13:
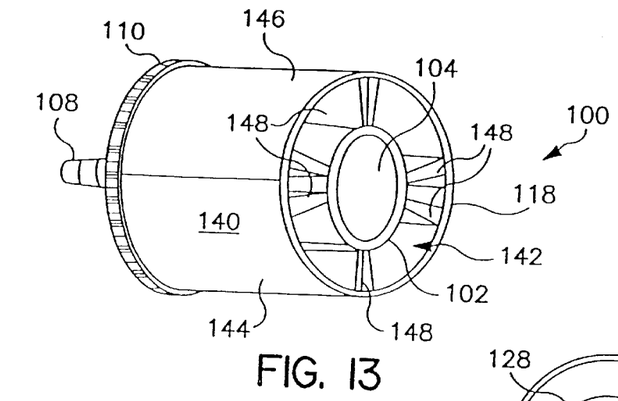
FIG. 13. is a perspective inlet end view of a flow control device in accordance with another embodiment of the invention.
Figure 14:
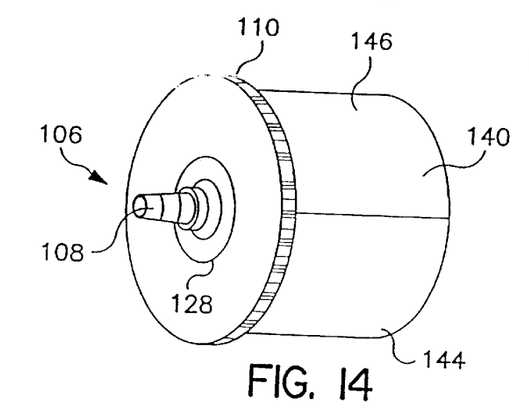
FIG. 14 is a perspective outlet end view of the device of FIG. 13.
Figure 15:
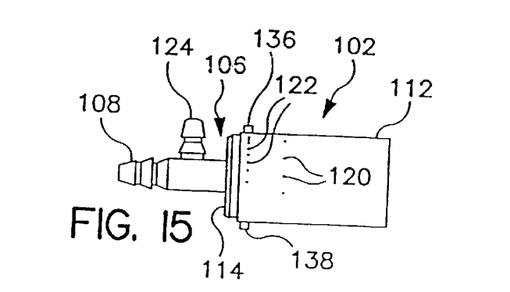
FIG. 15 is a side plan view of a flow member component of the device of FIG. 14.
Figure 16:
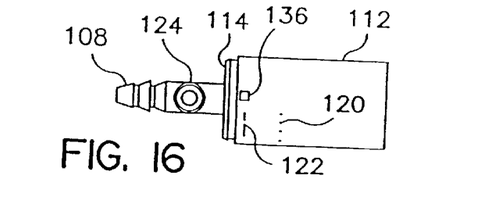
FIG. 16 is a top plan view of the component of FIG. 15.

The system 100 includes flow member 102 having an inlet end 104 placeable in flow communication with the source of warm, humidified oxygen and an opposite outlet end 106 in flow communication with a fitting 108 and placeable in flow communication with a cannula. A control member 110 cooperates with the flow member 102 for adjustably controlling the flow of humidified oxygen out of the fitting 108.

The flow member 102 is preferably provided by a conduit 112, an open end of which provides the inlet end 104. The opposite end of the conduit 112 is closed, as by end wall 114. The fitting 108 extends through the end wall 114 to provide a flow path for the warm, humidified oxygen. Cylindrical sidewall 118 of the conduit 112 is substantially solid with the exception of at least one aperture 120 and at least one aperture 122 which are spaced apart from one another and extend through the sidewall 118. The aperture 120 is preferably upstream of the aperture 122 and is preferably a circular aperture. The aperture 122 is preferably a circular aperture. An additional fitting 124 optionally extends from the fitting 108 for connection with a flow meter for measuring the flow rate of humidified oxygen being delivered to the patient. The exterior of the end wall 114 is preferably flanged to provide a snap-fit relationship with the control member 110 which permits relative rotation of the control member 110 and the flow member 102.

Figure 17:
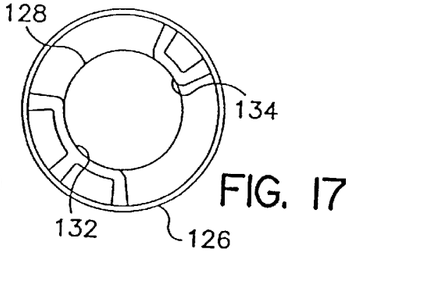
FIG. 17 is an inlet end view of a cap member component of the system of FIG. 13.
Figure 18:
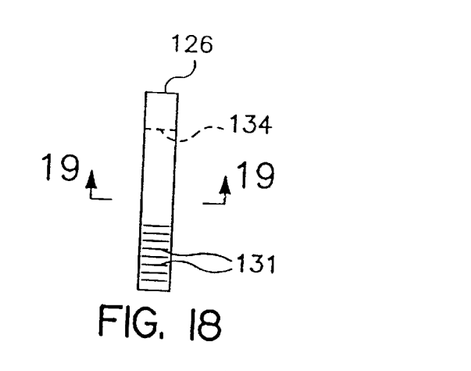
FIG. 18 is a side view of the component of FIG. 17.
Figure 19:
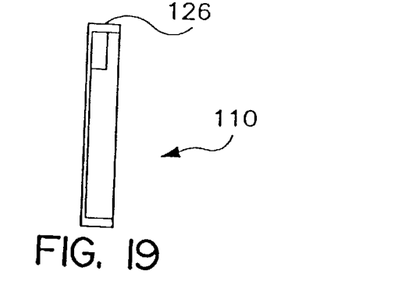
FIG. 19 is a cross-sectional view of FIG. 18 taken along line 19—19.

With reference to FIGS. 17–19, the control member 110 includes a cap member 126 including an aperture 128 centrally located and sized to receive the fitting 108 or the exterior of the end wall 114. The end wall thickness of the cap member 126 (FIG. 19) is sized to provide a snap-fit relationship with the flanged exterior of the end wall 114 of the flow member 102 to maintain the control member 110 and the flow member 102 adjacent one another. The circumference of the cap member 126 is preferably textured, such as knurls 131, to facilitate grasping thereof.

The cap member 110 includes projections 132 and 134 which extend from the interior circumference of the cap member 110 and rotatably engage opposite sides of the exterior of the conduit 102. The projection 132 is opposite the projection 134 so that a portion of the conduit is captured there between. The rotation of the cap member relative to the conduit is preferably limited by as by stops 136 and 138 located on the exterior of the conduit 102 for engaging the outside edges of the projection 132. The stops 136 and 138 are preferably located such that contact with the stop 132 defines the position of the projection 132 when it fully blocks the aperture 122 and contact with the stop 138 defines the position of the projection 132 when it fully clears the aperture 122.

A shroud 140 (FIGS. 13 and 14) is preferably provided to surround the conduit 102 to provide an annular area 142 there between sufficient to enable the flow of humidified oxygen from the flow member 102 through the apertures 120 and 122. The shroud 140 is preferably of two-piece construction and including a pair of half cylinders 144 and 146 which press fit together. A plurality of elongate baffle members 148 preferably extend between the interior of the shroud 140 and the exterior of the conduit 112 in the annular area 142 there between and are located so as to contact one or more of the apertures 120, as may be desired. The baffle members 148 are preferably co-formed with the half cylinders 144 and 146. The baffle members 148 function to selectively cover one or more of the apertures 120 and to disrupt and diffuse flow exiting the undercovered apertures 120 and 122. The shroud member 140 abuts the cap member 110 but is preferably not connected thereto.

The cap member 110 and the flow member 102 may be rotated relative to one another to selectively position the projection 132 relative to the aperture 122 in the manner previously described for projection 54 and aperture 40 of system 10 of FIGS. 1–12.

Figure 20:
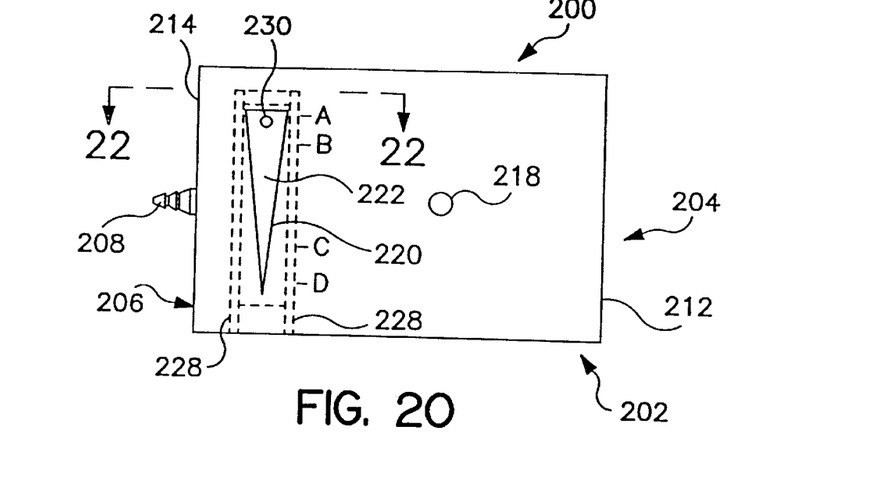
FIG. 20 is a side plan view of a flow control device in accordance with another embodiment of the invention.
Figure 21:
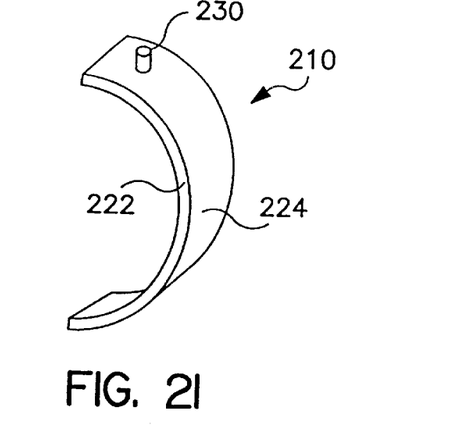
FIG. 21 is a perspective view of a flow control component of the device of FIG. 20.
Figure 22:
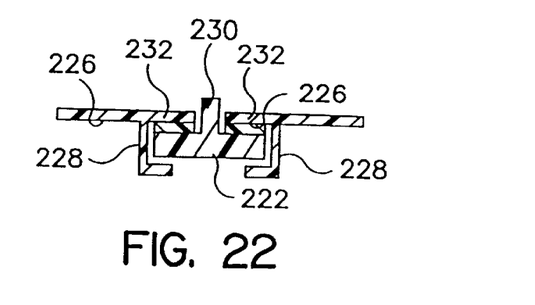
FIG. 22 is a partial cross-sectional view taken along line 22—22 of FIG. 20.

Turning now to FIGS. 20–22, there is shown another embodiment of a system 200 for controlling the flow rate of fluid, such as a gas-liquid mixture, from a source of fluid, such as a source of humidified oxygen for delivery to a patient as by a nasal cannula.

The system 200 includes a flow member 202 having an inlet end 204 placeable in flow communication with the source of humidified oxygen opposite an outlet end 206 in flow communication with a fitting 208 and placeable in flow communication with a cannula for delivery of the humidified oxygen to a patient. A control member 210 cooperates with the flow member 202 for adjustably controlling the flow of humidified oxygen out of the fitting 208.

The flow member 202 is preferably provided by a conduit 212, one open end of which provides the inlet end 204. The opposite end of the conduit 212 is closed, as by end wall 214. The fitting 208 extends through the end wall 214 to provide a flow path for the oxygen. The cylindrical sidewall of the conduit 212 is substantially solid with the exception of at least one aperture 218 and at least one aperture 220 which are spaced apart from one another and extend through the sidewall of the conduit 212. The aperture 218 is preferably upstream of the aperture 220 between aperture 220 and inlet end 204 and is preferably a circular aperture. The aperture 220 is preferably a triangular shaped aperture.

The control member 210 is preferably provided by a semi-circular member 222 having a width that is preferably at least as great as the largest width dimension of the aperture 220 and having a radius corresponding to the inner radius of the conduit 212 so that an outwardly facing surface 224 of the control member 210 will bear against interior sidewall 226 of the conduit 212.

As shown in FIG. 22, a pair of generally L-shaped channels 228 are preferably co-formed with the conduit 212 and extend circumferentially around the interior sidewall 226 of the conduit 212 for slidably receiving the semi-circular member 222. A stop 230 preferably extends from the surface 224 of the member 222 to engage the length extremes or edges of the aperture 220 and limit travel of the member 222. As will be appreciated, the member 222 may be slidably positioned to vary the flow rate of humidified oxygen through the aperture 220. That is, the stop 230 may be positioned at position A to substantially close the aperture 220 and provide a flow through the fitting 208 to the patient of about 2 liters per minute, at position B to substantially open the aperture 220 and provide a flow through the fitting 208 of about 0 liters per minute and at points there between, such as points C or D, to provide flow rates within the range of about 0 to about 2 liters per minute as may be desired. A gasket material, such as rubber strips 232 may be positioned between the member 222 and the sidewall 226 between the channels 228 to minimize leakage when the member 222 is positioned to seal the aperture 220 or a portion thereof.

FIGS. 23–29 show another embodiment of a system 300 for controlling the flow rate of humidified oxygen to patients including pediatric or infant patients. The system 300 includes a flow member 302 and a control member 304.

Figure 23:
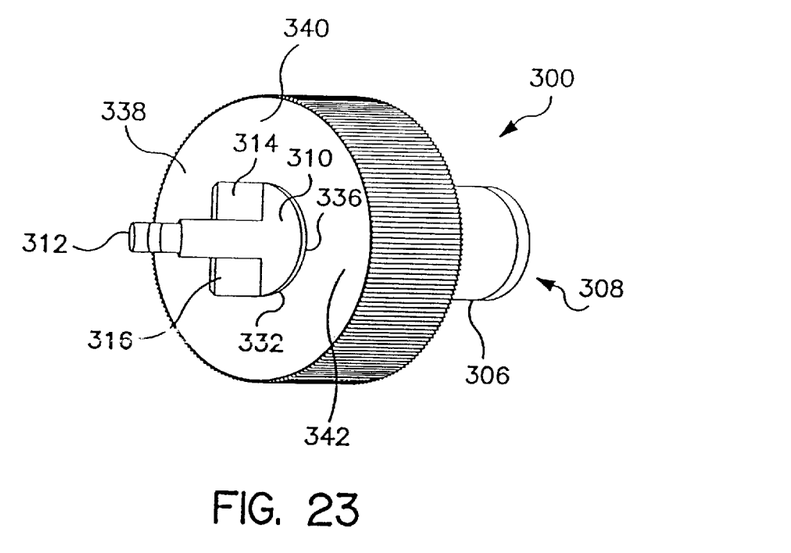
FIG. 23 is a front perspective view of a flow control system in accordance with yet another embodiment of the invention.
Figure 24:
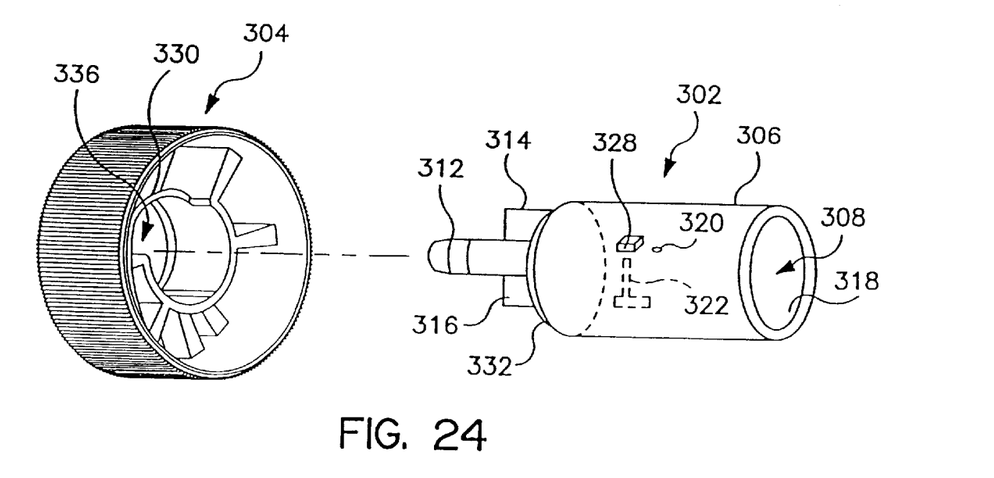
FIG. 24 is an exploded perspective view of the device of FIG. 23.
Figure 25:
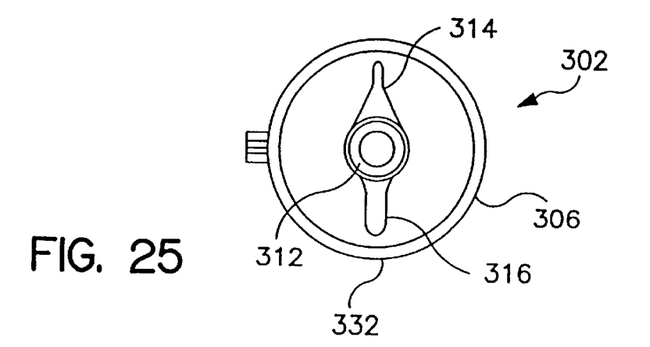
FIG. 25 is a front end view of a component of the device of FIG. 23.
Figure 26:
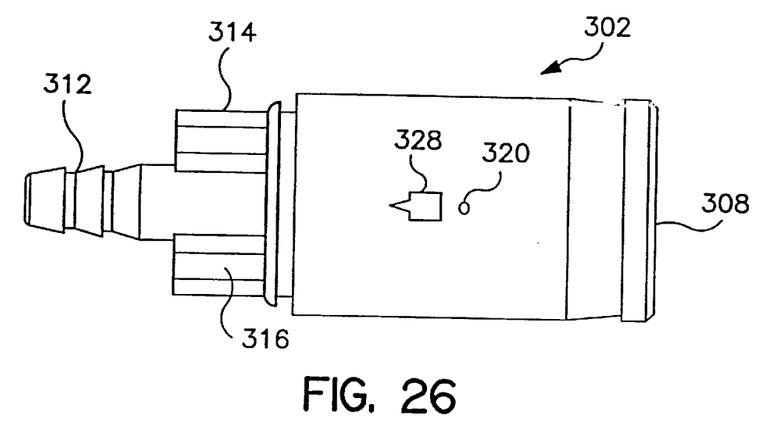
FIG. 26 is a left side view of the component of FIG. 25.
Figure 27:
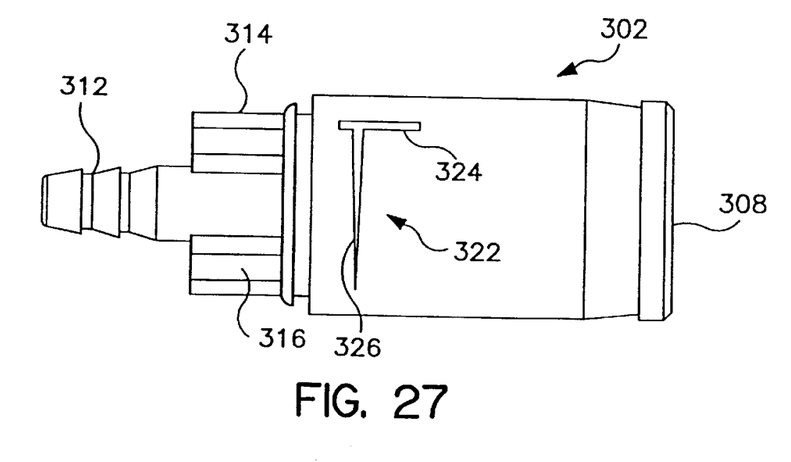
FIG. 27 is a right side view of the component of FIG. 25.

The flow member 302 is preferably provided by a conduit 306 having an open inlet end 308 placeable in flow communication with a source of warm, humidified oxygen. The opposite end of the of the conduit 306 is closed as by end wall 310. A fitting 312 connectable to a cannula and associated tubing extends through the end wall 310 to provide a flow path for the warm, humidified oxygen. To facilitate rotation of the conduit 306 relative to the control member 304 in the assembled system 300, a pair of wings 314 and 316 project from the fitting 312 adjacent the end wall 310 for grasping by a user.

Cylindrical sidewall 318 of the conduit 306 is substantially solid with the exception of apertures 320 and 322 which are spaced apart from one another and extend through the sidewall 318. The aperture 320 is upstream of the aperture 322 and is preferably a single circular aperture. The aperture 322 preferably includes a lateral slit portion 324 parallel to the length of the conduit 306 and a v-shaped slit 326 extending generally perpendicular to the slit portion 324 along the circumference of the conduit 306.

The control member 304 is configured to selectively engaging portions of the aperture 322 for controlling the area of the aperture 322 available to bleed off oxygen traveling through the conduit 306. In this connection, a projection 328 is preferably defined on the surface of the conduit 306 for selectively engaging notches 330 located on an interior surface of the control member 304 for facilitating incremental relative movement of the control member 304 and the conduit 306. To enable a snap-fit relationship between the conduit 306 and the control member 304, the end wall 310 of the conduit 306 preferably includes a flange 332 for engaging fingers 334 located adjacent an aperture 336 defined through end wall 338 of the control member 304 for passage of the end wall 310, the wings 314 and 316 and the fitting 312. Indicia 340 and 342 are preferably provided on the exterior of the end wall 338 for aligning with the wing 314 when the aperture is fully opened and fully closed, respectively. Likewise, the exterior surface of sidewall 343 of the control member 304 preferably includes knurls 344 for facilitating grasping by the user during adjustment of the system 300.

Figure 28:
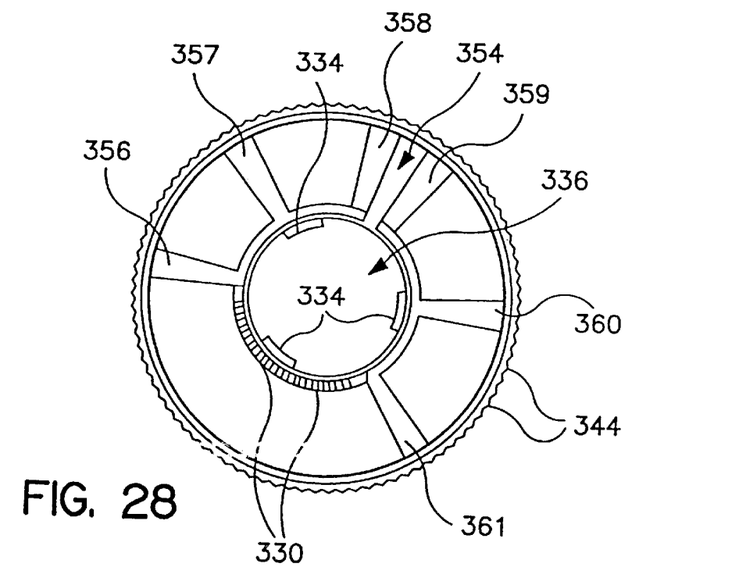
FIG. 28 is a rear plan view of another component of the device of FIG. 23.
Figure 29:
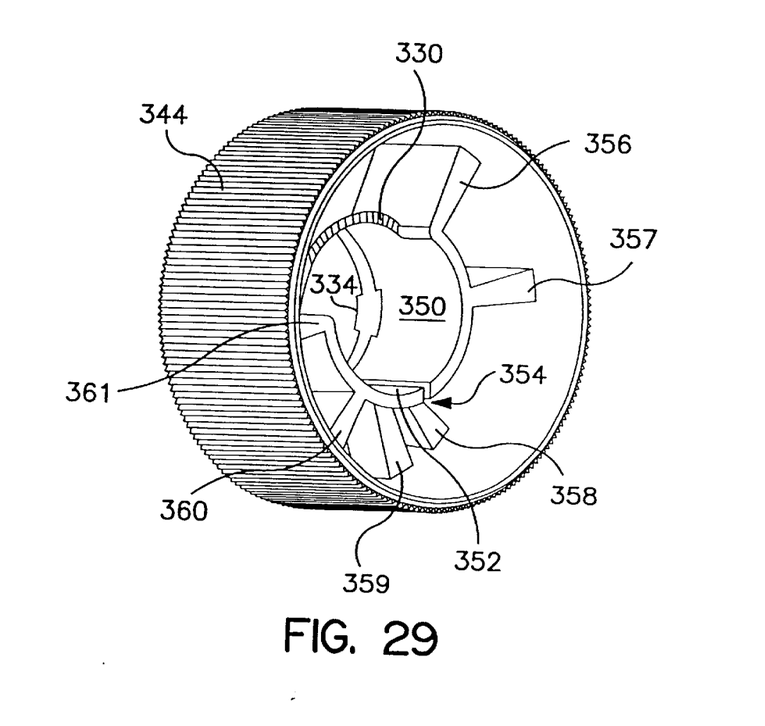
FIG. 29 is a rear perspective view of the component of FIG. 28.
Figure 30A:
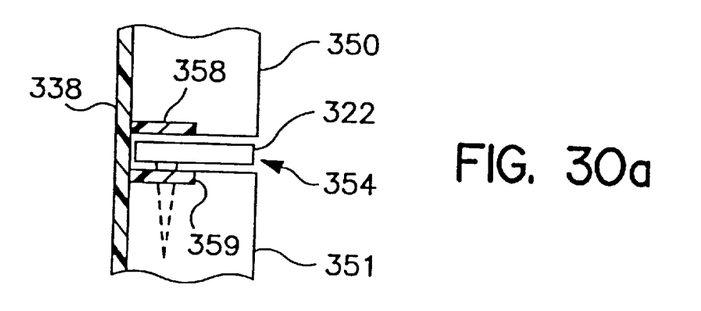
FIGS. 30a, 30b and 30c are detailed cross-sectional side views of the system of FIG. 23 showing the relationship between the flow component and the control component.
Figure 30B:
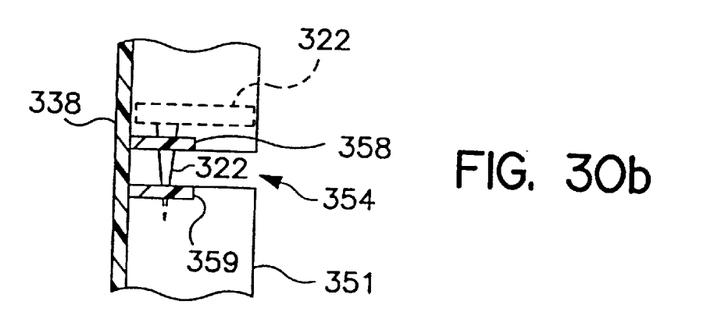
Figure 30C:
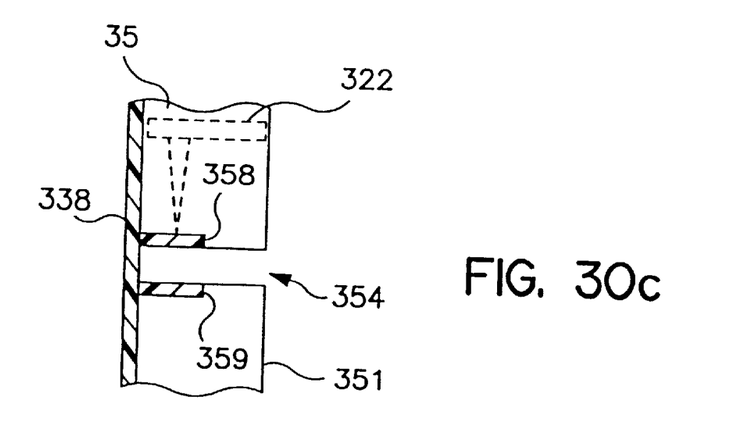

With reference to FIGS. 28 and 29, the control member includes interior cylindrical sidewalls 350 and 352 spaced apart by an open area or slot 354. As will be appreciated with reference to FIGS. 30a, 30b and 30c, the control member 304 and the conduit 306 may be moved relative to one another for selectively engaging portions of the aperture 322 for controlling the area of the aperture 322 available to bleed off oxygen traveling through the conduit 306.

Fingers 356, 357 and 358 project between the exterior of the sidewall 350, the interior of the end wall 338 and the interior of the conduit 306 for strength. Likewise, fingers 359, 360 and 361 project between the exterior of the sidewall 352, the interior of the sidewall 338 and the interior of the conduit 306. The fingers 357 and 358 are preferably of a lesser width than that of the slot 354 to enable escaping oxygen to expand relatively quickly and thereby reduce its velocity to reduce noise associated with the oxygen that is being bled off through the aperture 322.

For the purpose of an example, the conduit 306 may be dimensioned similar to that of the conduit or cylindrical member 30. For use with a source of warm, humid oxygen having an output of about 8 liters/minute, the aperture 320 preferably has a diameter of about 0.04 inches, so that it may leak or bleed a flow rate of about 6 liters per minute there through. The lateral slit 324 preferably has a length of about 0.33 inches and a length of about 0.52 inches. The v-shaped slit 326 preferably extends about 105° around the circumference of the conduit 306 and tapers in width from about 0.55 inches adjacent the slit 324 to about 0.01 inches at its tip. The slot 354 of the cover member 304 preferably tapers outwardly over the thickness of the sidewall 350 (about 0.55 inches, for example), with slot 354 preferably having an initial width of about 0.3 inches and a terminal width of about 0.5 inches.

FIGS. 31–36 show another embodiment of a system 400 for controlling the flow rate of humidified oxygen to patients including pediatric or infant patients. The system 400 includes a flow member 402 and a control member 404.

Figures 31, 32:
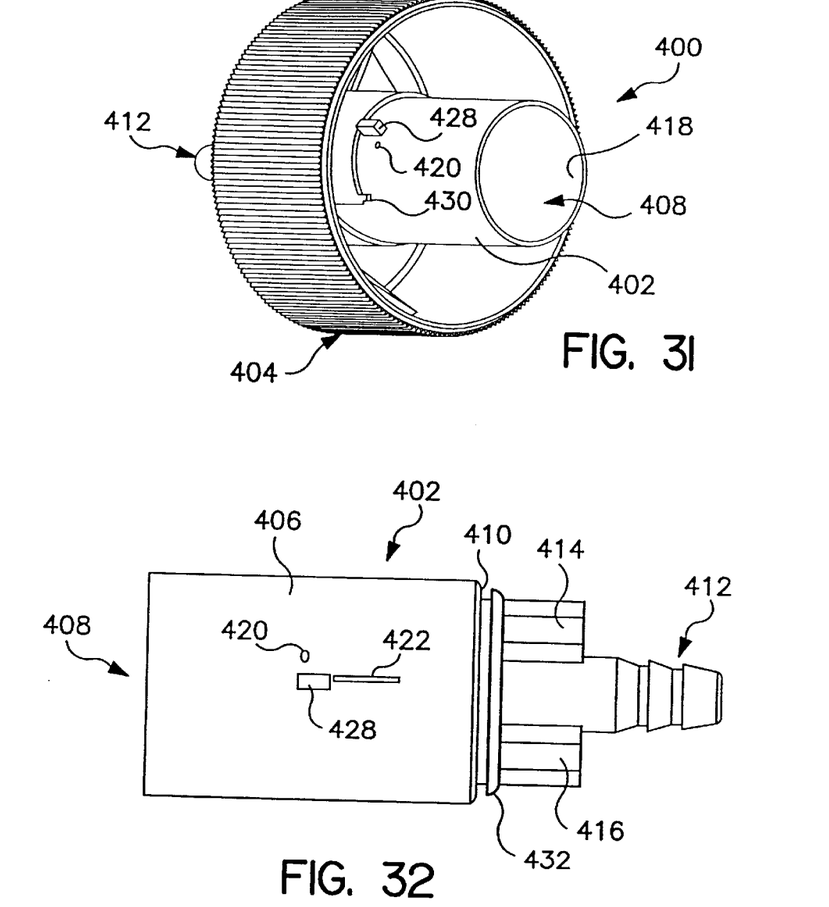
FIG. 31 is a rear perspective view of a flow control system in accordance with still another embodiment of the invention.
FIG. 32 is a side plan view of another component of the flow control system of FIG. 31.
Figure 33:
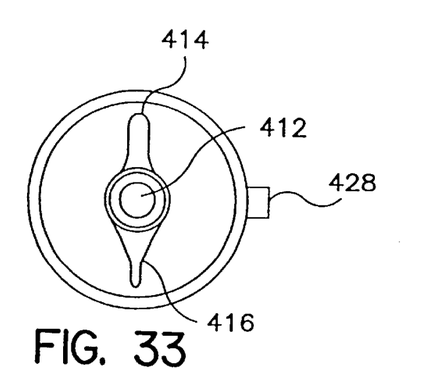
FIG. 33 is a front end view of the component of FIG. 34.
Figure 34:
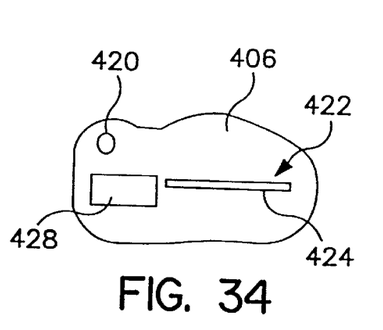
FIG. 34 is a close-up view of a portion of the component of FIG. 34.

The flow member 402 is preferably provided by a conduit 406 having an open inlet end 408 placeable in flow communication with a source of warm, humidified oxygen. The opposite end of the of the conduit 406 is closed as by end wall 410. A fitting 412 connectable to a cannula and associated tubing extends through the end wall 410 to provide a flow path for the warm, humidified oxygen. To facilitate rotation of the conduit 406 relative to the control member 404 in the assembled system 400, a pair of wings 414 and 416 project from the fitting 412 adjacent the end wall 410 for grasping by a user.

Cylindrical sidewall 418 of the conduit 406 is substantially solid with the exception of apertures 420 and 422 which are spaced apart from one another and extend through the sidewall 418. The aperture 420 is upstream of the aperture 422 and is preferably a single circular aperture. The aperture 422 is preferably a lateral slit 424 having a length axis parallel to the length of the conduit 406.

Figure 35A:
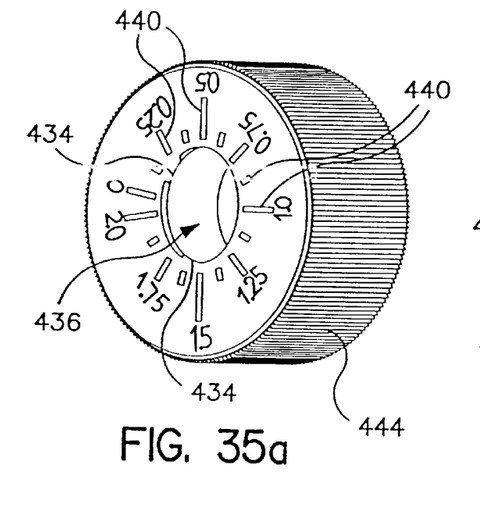
FIGS. 35a and 35b are front and rear perspective views, respectively, of a component of the flow control system of FIG. 31.
Figure 35B:
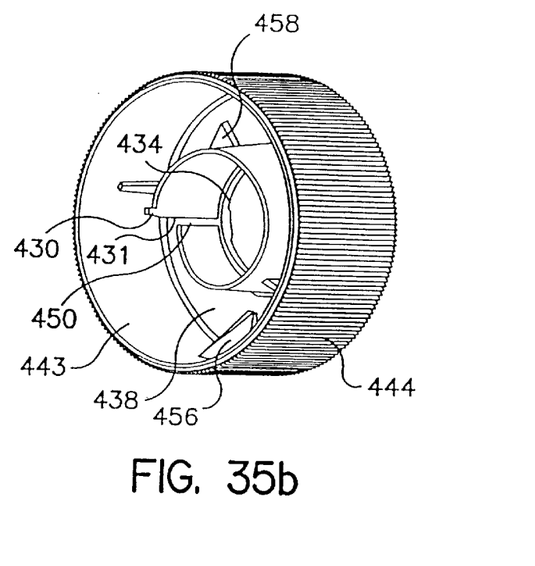
Figure 36:
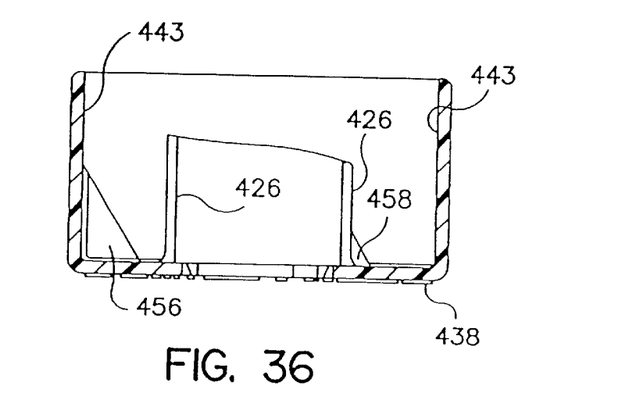
FIG. 36 is a cross-sectional side view of the component of FIGS. 35a and 35b.

The control member 404 is configured to selectively engaging portions of the aperture 422 for controlling the area of the aperture 422 available to bleed off oxygen traveling through the conduit 406. In this connection, a spiraled interior sidewall 426 is provided on the control member 404. A projection 428 is preferably defined on the surface of the conduit 406 for selectively engaging either a notch 430 defined along an uppermost edge of the sidewall 426 or a side edge 431 of the sidewall 426. As will be appreciated, the notch 430 and the edge 431 define the limits of travel of the projection 428.

To enable a snap-fit relationship between the conduit 406 and the control member 404, the end wall 410 of the conduit 406 preferably includes a flange 432 for engaging fingers 434 located adjacent an aperture 436 defined through end wall 438 of the control member 404 for passage of the end wall 410, the wings 414 and 416 and the fitting 412. Indicia 440 is preferably provided on the exterior of the end wall 438 for aligning with the wing 414 or 416 to indicate the degree to which the aperture or slit 422 is opened or closed or the approximate flowrate of gas being delivered to the patient. Likewise, the exterior surface of sidewall 443 of the control member 404 preferably includes knurls 444 for facilitating grasping by the user during adjustment of the system 400.

Figure 37A:
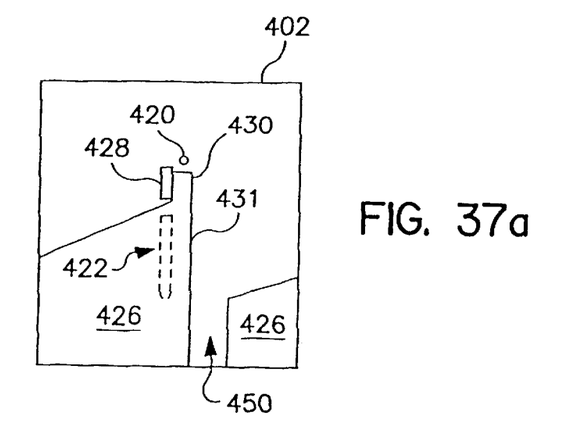
FIGS. 37a, 37b and 37c are cross-sectional side views of the system of FIG. 31 showing the relationship between the flow component and the control component.
Figure 37B:
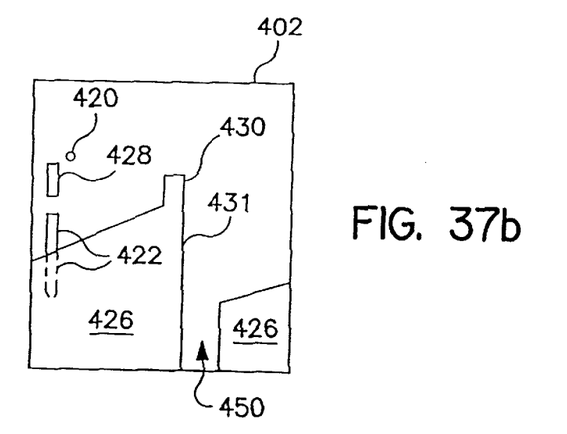
Figure 37C:
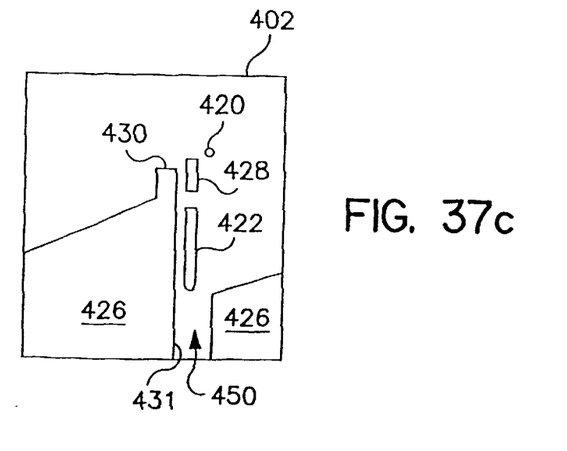

An open area or slot 450 is located between side edge 431 and an opposite side edge 452 of the spiraled sidewall 426. As will be appreciated with reference to FIGS. 37a, 37b and 37c, the control member 304 and the conduit 306 may be moved relative to one another for selectively engaging portions of the aperture 322 for controlling the area of the aperture 322 available to bleed off oxygen traveling through the conduit 306. For example, the aperture 422 is totally blocked in FIG. 37a; partially blocked in FIG. 37b and totally unblocked in FIG. 37c.

Reinforcing members 456 and 458 are provided to reinforce the sidewalls 443 and 426, respectively. The members 456 and 458 are preferably flat, having a triangular outline. One leg of each member is against to the interior of the sidewall it is reinforcing and the other leg is against the interior of end wall 438.

For the purpose of an example, the conduit 406 may be dimensioned similar to that of the conduit 306. For use with a source of warm, humid oxygen having an output of about 8 liters/minute, the aperture 420 preferably has a diameter of about 0.04 inches, so that it may leak or bleed a flow rate of about 6 liters per minute there through. The lateral slit 424 preferably has a length of about 0.30 inches and a width of about 0.011 inches.

The spiraled sidewall 426 preferably increases in height in a cubic function to help linearize the air flow through the slit 424 as a function of the relative position of the flow member 402 and the control member 404. The height difference between the lowest and highest portions of the sidewall is preferably about 0.3 inches so that the end ranges of relative rotation of the flow member and the control member represent the slit 424 being fully blocked or fully open. The spiraled sidewall 426 preferably has a diameter of about 0.4 inches (the member 404 having an outer diameter of about 2 inches).

As will be appreciated, the invention enables warm, humidified oxygen to be delivered to patients in a manner which has not previously been possible. For example, limitations in the design of conventional equipment for providing warm, humid oxygen requires that they be operated at flow rates that are generally greater than the desired flow rate that the oxygen be delivered to the patients such as pediatric and infant patients and many elderly patients. Furthermore, to avoid problems with overheating and the like, such equipment should, practically speaking, be operated at flow rates significantly greater than its minimum possible operating flow rate.

The invention interfaces between conventional humidification equipment and its normal operating parameters to enable warm, humidified oxygen to be delivered at the very low flow rates often required for various patients. Thus, the humidification equipment can be operated at conditions which avoid overheating and other problems, yet the patient is able to receive very low flow rates of the warm, humid oxygen. Accordingly, the invention satisfies a long felt need in the art in a convenient and efficient manner.

The foregoing description of certain embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A system for delivering a flow of humidified oxygen to a patient at a flow rate of from about 2 liters per minute to about ⅛ liter per minute, the system comprising: a source of humidified oxygen having a flow rate of from about 3 to about 15 liters per minute; a conduit having an inlet in flow communication with the source of the humidified oxygen and an outlet for delivering the oxygen composition to the patient at a flow rate of from about 2 liters per minute to about ⅛ liter per minute; a first flowpath extending through a sidewall of the conduit and in flow communication with the atmosphere, the first flowpath being configured to continuously bleed a first desired amount of the flow of the humidified oxygen from the conduit to the atmosphere without changing the oxygen composition within the conduit to provide a flow of humidified oxygen in the conduit downstream of the first flowpath at a flow rate of about 2 liters per minute; a second flowpath downstream from the first flowpath and extending through the sidewall of the conduit and in flow communication with the atmosphere, the second flow path being configured to continuously bleed a second desired amount of the flow of the humidified oxygen from the conduit to the atmosphere at a rate of from about 0 liters/minute or above without changing the oxygen composition within the conduit to provide flow of the humidified oxygen in the conduit downstream of the second flowpath at a flow rate of from about 2 liters per minute to about ⅛ liters per minute and a substantially solid member movably positionable adjacent the second flowpath for selectively blocking and unblocking portions of the second flowpath for defining a variably dimensionable flow path in order to provide control over the amount of the flow of the humidified oxygen flowing through the second flowpath without changing the oxygen composition of the flow of the humidified oxygen as it travels from the source to the patient.

* * * * *